US005547963A

United States Patent [19]
Poindron et al.

[11] Patent Number: 5,547,963
[45] Date of Patent: Aug. 20, 1996

[54] METHOD FOR STIMULATING NERVE REGENERATION

[75] Inventors: Philippe Poindron; Serge Braun, both of Illkirch Cedex; Badia Ferzaz, Antony, all of France

[73] Assignee: Synthelabo, Le Plessis Robinson, France

[21] Appl. No.: 508,458

[22] Filed: Jul. 28, 1995

Related U.S. Application Data

[63] Continuation of Ser. No. 230,930, Apr. 21, 1994, abandoned.

[30] Foreign Application Priority Data

Mar. 9, 1994 [FR] France ................................. 94 02699

[51] Int. Cl.⁶ ..................................................... A61K 31/445
[52] U.S. Cl. ............................................ 514/317; 514/903
[58] Field of Search ..................................... 514/317, 903

[56] References Cited

U.S. PATENT DOCUMENTS

| 4,690,931 | 9/1987 | Wick et al. | 514/317 |
| 5,023,266 | 6/1991 | Langer et al. | 514/317 |

*Primary Examiner*—Marianne M. Cintins
*Assistant Examiner*—M. Moezie
*Attorney, Agent, or Firm*—Jacobson, Price, Holman & Stern, PLLC

[57] ABSTRACT

Use of eliprodil and its enantiomers for the preparation of medicines useful for the treatment of peripheral nouropathies and chronic neurodegenerative diseases of the central nervous system.

1 Claim, No Drawings

METHOD FOR STIMULATING NERVE REGENERATION

This application is a continuation of application Ser. No. 08/230,930, filed Apr. 21, 1994 now abandoned.

The present invention concerns the use of eliprodil and its enantiomers for the preparation of medicines useful for the treatment of peripheral neuropathies and central neurodegenerative diseases.

Eliprodil is a compound with the following structure:

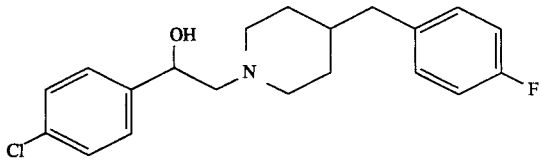

It has well characterised neuroprotective properties which have been described in European patent no 0 109 317.

This compound also possesses antipsychotic activity as described in European patent no 0 428 438.

Eliprodil and its enantiomers have undergone new pharmacological studies which have demonstrated their neurotrophic properties.

More specifically, the stimulation by eliprodil and its enantiomers of neurite outgrowth and synapse formation has been demonstrated in mixed cultures of human muscle fibres and rat spinal cord neurons.

This study was carried out as follows:

Human muscle fragments, cleared of their fibrous sheath, were cut into small pieces and incubated overnight in a conditioning medium consisting of 199 medium with 10% fetal calf serum (FCS) and 1% of a ready-to-use antibiotic and antifungic solution (sodium benzylpenicillinate, streptomycin, fungizone [GIBCO]). These fragments were maintained in a nourishing coagulum consisting of 4 volumes of conditioning medium and 1 volume of human plasma. Explants were then transferred into gelatin-coated Petri dishes, humidified and immobilised on the support by incubation for 1 h at 37° C. and F14 medium (GIBCO), containing 10% FCS, 2 mM glutamine, 10 µg/ml insulin, 10 ng/ml FGF and 10 ng/ml EGF, was added. A large number of satellite muscle cells (precursors of muscular fibres in the adult) migrate outside the explants. These cells start to proliferate and to merge after 1 week in culture. Explants were removed before the satellite cells merged into myotubes. Cells were treated with trypsin just before the merging phase and subculture in order to obtain the amount required for the experiments.

Cells were finally seeded (20.000/cm$^2$). After formation of myotubes, spinal cord explants from 13 day-old rat embryos were immobilized over the muscular cell layer and co-cultured in 25% 199 medium, 67.5% MEM medium (GIBCO), 5% FCS, 10 µg/ml insulin and 1% antibiotic solution. This culture medium was renewed twice a week. Test compounds were dissolved in this culture medium.

With this co-culture technique, all the spinal cord explants form neurites, but not all succeed in innervating muscle cells and inducing their contraction. Such a contraction is an indication of successful innervation. Under standard conditions, only 1 out of 4 explants is able to establish functional contacts with muscle fibres. Thus, these experimental conditions are optimal for the demonstration of neuritogenesis and synapse formation.

The effects of test compounds were determined at concentrations of $10^{-11}$, $10^{-9}$, $10^{-7}$ and $10^{-6}$M, after 3–4 weeks of treatment in comparison with the vehicle (0.1% ethanol for the highest concentration). The following parameters were measured:

1) Neurite length

Neurite length was determined by using a phase-contrast microscope (final magnification×200) with an ocular micrometer. Neurite length was measured from the centre of the explant without taking into account the curving of these filamentous extensions. The length of the branchings was also measured. The total neurite length was determined in at least 15 explants.

2) Number of neurites per explant

The number of neurites emerging from each explant was determined without taking into account the branchings.

3) Number of neuromuscular junctions

Counting of cholinergic receptor aggregates

Cultures were incubated for 1 h in the presence of $^{125}$I-α-bungarotoxin, fixed with 2.5% glutaraldehyde, dried and dipped in a fluid photographic emulsion. Autoradiograms were developed after 10 days of exposure. Cultures were examined under a microscope (magnification×200) in order to select isolated muscular fibres with clearly distinct receptor aggregates (these fibres are in general larger than the diameter of the microscope field, and the length of this field is taken as the length unit). At least 60 fibres were studied. Values are the mean of the number of aggregates multiplied by a correction factor and are expressed in mm.

Number of acetylcholinesterase-rich synaptic zones

Acetylcholinesterase was revealed by the technique of Karnovsky and Roots as modified by Kobayashi and Askanas (J. Neurosci, vol 7, 3131–3141, 1987). Acetylcholinesterase-rich synaptic zones were counted according to the technique described above for receptor aggregates, and had a similar distribution and number.

4) Surface of the innervated zones

Total surface of the innervated muscular cell areas around the explant.

This parameter corresponds to the area covered by the motor neurons without taking into account the presence of non innervated zones or other cellular types inside this area.

Actual surface covered by innervated muscular fibres

This area is determined by either autoradiographic detection of cholinergic receptor aggregates or by acetylcholinesterase staining and is quantified, after digitalization, by using an image analyzer. This parameter gives an estimation of the number of innervated muscle fibres.

It was found that eliprodil and its enantiomers enhance neuritic outgrowth, from the concentration of $10^{-7}$M, in both innervating and non innervating explants. At this eliprodil concentration, the mean increase in neurite length was 25% and 28% for innervating and non innervating explants, respectively.

Eliprodil also increased the number of neurites. At $10^{-6}$M, the mean increase was 156% in explants giving rise to innervation and 100% for explants that did not give rise to innervation in explants.

From $10^{-7}$M, this compound also increased, the number of neuromuscular junctions and the muscular fibre innervated surface. At $10^{-6}$M, there was an increase of 60% in the number of neuromuscular junctions and an increase of 116 and 142% in the total and the actual innervated surface of muscular fibres, respectively.

Likewise, at the concentration of $10^{-7}$M, the S(+) and R(−) enantiomers of eliprodil increased by 68 and 32%, respectively, the neurite length in the innervated areas and by 126 and 162%, respectively, the number of neurites in explants giving rise to innervation.

The effects of eliprodil on the regeneration of the sciatic nerve in the rat was also studied in vivo after a local freezing lesion.

Freezing lesion destroys sciatic nerve fibres and results in a wallerian degeneration both at the site of the lesion and in more distal parts. This kind of lesion does not alter the nerve sheaths allowing for reproducible nerve regeneration.

The regeneration process begins on the proximal side a few hours after the lesion.

The rate of regeneration of sensory fibres was measured by a pinch-test 8 days after the lesion.

Adult male rats (250 g body weight) of the Sprague-Dawley strain were used. Rats were anaesthetized with sodium pentobarbital (60 mg/kg), the thigh skin was disinfected with ethanol and an incision was made at the level of the junction of femoral biceps. The sciatic nerve was approached by separating the Lateralis and Biceps femoralis muscles. The site of the lesion was identifed with a microsuture (Black Ethilon thread 10-0) performed on perineurium above the trifurcation of the sciatic nerve. The nerve was lesioned by 6 freezing and thawing cycles using a copper cryode cooled in liquid nitrogen. The wound was closed and treated with an antibiotic (Exoseptoplix®). Animals were housed one per cage and watched over every day.

After surgery, rats were separated into 4 experimental groups of 6 animals each:

lesioned controls receiving an ip injection of 0.1% Tween 80 twice a day lesioned controls receiving an ip injection of 0.1% Tween 80 every 3 days lesioned animals receiving an injection of 1 mg/kg ip of eliprodil twice a day lesioned animals receiving an injection of 10 mg/kg ip of eliprodil every 3 days Eight days after surgery, rats were lightly anaesthetized and the sciatic nerve was exposed in order to carry out the pinch test. This test consists of gently pinching the nerve with forceps every 0.5 mm starting from the most distal region from the lesion. A reflex response (contraction of the hindlimb muscles) was observed when pinching at the front of the regenerating sensory fibres. After identifying this site with a microsuture, the nerve was dissected out and the distance between the site of the lesion and the distal microsuture was measured under a surgical microscope using a calibrated paper. After dissection, rats were sacrificed by a pentobarbital overdose.

In untreated lesioned animals, a response to pinch test was observed at a distance of 25 mm from the lesion site 8 days after surgery; this length corresponds to the distance travelled by the regenerating sensory fibres during this time. This distance was the same for rats treated twice a day and those treated every 3 days with Tween 80. In rats treated with eliprodil twice a day at the dose of 1 mg/kg ip the distance travelled by sensory fibres was increased by 14%. In rats treated at the dose of 10 mg/kg ip every three days, this increase was 10%.

These results demonstrate that, in vivo, eliprodil stimulates the regeneration of the lesioned sciatic nerve.

Taken together, the results of these pharmacological studies performed both in vitro and in vivo indicate that eliprodil and its enantiomers favour the growth, repair and regeneration of neuronal axons and enhance the formation of neuromuscular junctions. These compounds can thus be used for the treatment of peripheral neuropathies such as traumatic (nerve severing or crushing), ischemic, metabolic (diabetes, uraemia), infectious, alcoholic, iatrogenic, genetic . . . etc neuropathies, in diseases involving motor neurons such as spinal amyotrophies and amyotrophic lateral sclerosis and also in the treatment of chronic neurodegenerative diseases involving a degeneration of central nervous system axons (Alzheimer's disease, Parkinson's disease, Multiple sclerosis).

Eliprodil and its enantiomers can be used in any galenic form, in association with appropriate excipients for oral, parenteral or local administration, for example as tablets, capsules, solutions, transdermal patches, in order to permit the administration of a daily dose of 1 to 30 mg of the active substance.

We claim:

1. A method of stimulating nerve regeneration in a mammal in need ther comprising administering to the mammal a therapeutically effective amount of eliprodil or an enantiomer thereof.

* * * * *